(12) United States Patent
Okun

(10) Patent No.: US 8,703,491 B2
(45) Date of Patent: *Apr. 22, 2014

(54) METHODS FOR MULTIPLEXED SAMPLE ANALYSIS

(71) Applicant: Vivia Biotech S.L., Tres Cantos-Madrid (SR)

(72) Inventor: Alex Okun, San Diego, CA (US)

(73) Assignee: Vivia Biotech S.L., Valladolid (ES)

( * ) Notice: Subject to any disclaimer, the term of this patent is extended or adjusted under 35 U.S.C. 154(b) by 0 days.

This patent is subject to a terminal disclaimer.

(21) Appl. No.: 13/679,977

(22) Filed: Nov. 16, 2012

(65) Prior Publication Data

US 2013/0109101 A1    May 2, 2013

Related U.S. Application Data

(60) Continuation of application No. 12/265,610, filed on Nov. 5, 2008, now Pat. No. 8,313,948, which is a division of application No. 11/683,829, filed on Mar. 8, 2007, now Pat. No. 7,459,126.

(60) Provisional application No. 60/781,103, filed on Mar. 10, 2006.

(51) Int. Cl.
*G01N 21/05* (2006.01)
*G01N 1/10* (2006.01)
*G01N 35/10* (2006.01)

(52) U.S. Cl.
USPC .................. 436/43; 436/52; 436/53; 436/54; 356/336; 422/63; 422/68.1; 422/70; 422/73; 422/501

(58) Field of Classification Search
None
See application file for complete search history.

(56) References Cited

U.S. PATENT DOCUMENTS

| | | | |
|---|---|---|---|
| 3,921,439 A * | 11/1975 | Burns | 73/61.41 |
| 4,680,270 A | 7/1987 | Mitsumaki et al. | |
| 5,174,162 A | 12/1992 | Miyake et al. | |
| 5,182,617 A | 1/1993 | Yoneyama et al. | |
| 5,308,583 A | 5/1994 | Sanuki | |
| 5,464,752 A | 11/1995 | Kortright et al. | |
| 5,695,720 A | 12/1997 | Wade et al. | |
| 5,895,764 A | 4/1999 | Sklar et al. | |
| 6,315,952 B1 | 11/2001 | Sklar et al. | |
| 6,638,481 B2 | 10/2003 | Sklar et al. | |
| 6,890,487 B1 | 5/2005 | Sklar et al. | |
| 7,198,956 B2 | 4/2007 | Uffenheimer et al. | |
| 2002/0086340 A1 | 7/2002 | Veerapandian et al. | |
| 2005/0009060 A1 | 1/2005 | Beernink et al. | |

FOREIGN PATENT DOCUMENTS

GB      1490107      10/1977

* cited by examiner

*Primary Examiner* — Kathryn Wright
(74) *Attorney, Agent, or Firm* — Knobbe Martens Olson & Bear LLP

(57) ABSTRACT

Disclosed herein is a sample supply device that alternates between the supply of samples from one sample line while cleaning a second sample line and then supplying a second sample from the second sample line while cleaning the first sample line. This is repeated in rapid succession to allow greater speed in analyzing a plurality of samples in a shorter amount of time.

8 Claims, 8 Drawing Sheets

METHODS FOR MULTIPLEXED SAMPLE ANALYSIS

CROSS-REFERENCE TO RELATED APPLICATIONS

This application is a continuation of U.S. patent application Ser. No. 12/265,610, filed on Nov. 5, 2008, which is a divisional of U.S. patent application Ser. No. 11/683,829, filed on Mar. 8, 2007, which claims priority to U.S. Provisional Application No. 60/781,103, filed on Mar. 10, 2006, the contents of which are hereby incorporated by reference in their entirety.

BACKGROUND OF THE INVENTION

1. Field of the Invention

This invention relates to a sample supply device for supplying an inspection instrument, such as a flow cytometer, with a plurality of samples at high speed.

2. Description of the Related Art

Traditionally, sample supply to the inspection cuvette of a flow cytometer has been accomplished by pressurizing a tube containing a sample to be analyzed, causing the sample to flow into the sample supply line. Automation of this traditional supply method is difficult due to mechanical issues with automatic positioning and sealing of sample containers. Such a supply method is also prone to creating aerosols of biohazardous materials.

Another method of sample supply, which is sometimes implemented in flow cytometers, is aspiration of sample into the flow cytometer syringe pump and then expulsion of the sample into flow cytometer cuvette. One drawback of this method is that pulsations created in the sample flow can greatly amplify noise on the measured signal. Additionally, the amount of time required for washing between samples is great and slows the process for analyzing samples. The washing process cannot begin until sample has been fully dispensed into the flow cytometer cuvette, resulting in reduced throughput.

Another method of sample supply is described in U.S. Pat. No. 5,182,617, which is herein incorporated by reference in its entirety. The '617 patent discloses that higher throughput may be achieved by creating two identical branches that can perform simultaneous sample introduction and washing. When used, analyzed samples stick to the channels of the system, including the interface channels, causing major carryover issues in subsequent sample analysis. The prior art provides no provision for thorough washing of an interface channel between the sample supply device and the flow cytometer. Furthermore, the prior art fails to teach any provision for rapidly washing the system with a cleaning liquid.

SUMMARY OF THE INVENTION

A method for multiplexed sample analysis is provided comprising the steps of (a) robotically obtaining a first liquid sample from the first of a plurality of sample sources; (b) delivering the first liquid sample through a first line to an instrument for analysis of the sample (c) robotically obtaining a second liquid sample from the second of a plurality of sample sources; (d) delivering the second liquid sample through a second line to an instrument for analysis; (e) cleaning the second line while the first line is delivering sample to the instrument; and (f) cleaning the first line while the second line is delivering sample to the instrument. In one embodiment, the method further comprises step (g) repeating steps (a)-(f) to obtain and deliver multiple samples to the instrument from all of the plurality of sample sources. Preferably, the instrument is a flow cytometer. In another embodiment, the instrument is selected from the group consisting of a spectrofluorometer, a fluorometer, an absorbance meter, and a microscope.

In an embodiment, the first and second liquid samples that are analyzed by the inspection instrument may be independently selected from the group consisting of chemical compounds, antibodies, beads, live cells, or fixed cells. Any sample typically analyzed by a flow cytometer, HPLC, spectrofluorometer, fluorometer, absorbance meter, microscope, or other high-throughput-instrument that receives liquid samples may be used.

In another embodiment, the method further comprises the steps of delivering a first reagent to the first liquid sample before the sample is delivered to the instrument and delivering a second reagent to the second liquid sample before the sample is delivered to the instrument. The first and second reagents may be independently selected from the group consisting of chemical compounds, antibodies, beads, live cells, or fixed cells. In still another embodiment, multiple reagents may be added to the sample before the sample is injected into the instrument.

In another embodiment, a control valve alternates delivery of cleaning fluid with the delivery of liquid sample in each of the first and second lines. The control valve may be connected to additional lines. Such lines may further provide the delivery of air pressure or system liquid pressure. Additionally, such lines may further provide a waste channel.

An apparatus for delivering samples to an instrument for analysis is provided comprising a first and a second sample delivery line, wherein the first sample delivery line comprises a first sample loading and injection branch and the second sample delivery line comprises a second sample loading and injection branch; a fluid flow management mechanism for alternately connecting the first and second sample delivery lines to the instrument; at least one cleaning fluid delivery line to supply cleaning fluid to the flow management mechanism, the first sample delivery line, and the second sample delivery line; at least one sample input channel; at least one control valve for alternately delivering cleaning fluid to the first and second sample delivery lines, so that sample and cleaning fluid alternately flow through the first and second sample delivery lines. In one embodiment, the at least one cleaning fluid delivery line supplies cleaning fluid to the entire system, including the inspection instrument.

In another embodiment, the fluid flow management mechanism comprises a position switching valve. The position switching valve may comprise a four-way two-position switching valve. The two-position switching valve may comprise two modes. In one embodiment, the first mode of the position switching valve fluidically couples the first sample delivery line to the instrument and fluidically couples the second sample delivery line to the sample input channel. In another embodiment, the second mode of the position switching valve fluidically couples the first sample delivery line to the sample input channel and fluidically couples the second sample delivery line to the instrument.

In one embodiment, the sample loading and injection branches of the first and second sample delivery lines comprise symmetrical sample loading and injection branches. In another embodiment, the first sample delivery line comprises a first sample holding loop and the second sample delivery line comprises a second sample holding loop. In another embodiment, a first control valve is located within the first sample delivery line and a second control valve is located within the second sample delivery line. In some embodiments, the first and second control valves each comprise four fluidic channels capable of coupling the first and second sample holding loops to one of the four fluidic channels. These additional fluidic channels may be connected to output ports of pump flow control valves, at least one cleaning fluid delivery line, waste disposal, or a controlled air pressure source.

DETAILED DESCRIPTION OF THE PREFERRED EMBODIMENT

The term "pressurizing means" as used herein refers to a variety of methods for providing pressure into the channels of the device. Non-limiting examples of pressurizing means include regulated compressed air from a tank, a regulated air compressor, and a syringe pump.

The term "storage means" as used herein refers to a variety of sample containers from which sample is aspirated into the sample supply channel. Non-limiting examples of storage means include a 96, 384, or 1536 well plate or a rack comprising any number of test tubes.

The term "channel switching means" as used herein refers to a switching valve that directs fluid in the channels to desired locations in the device of any embodiment disclosed herein.

Figure 1:
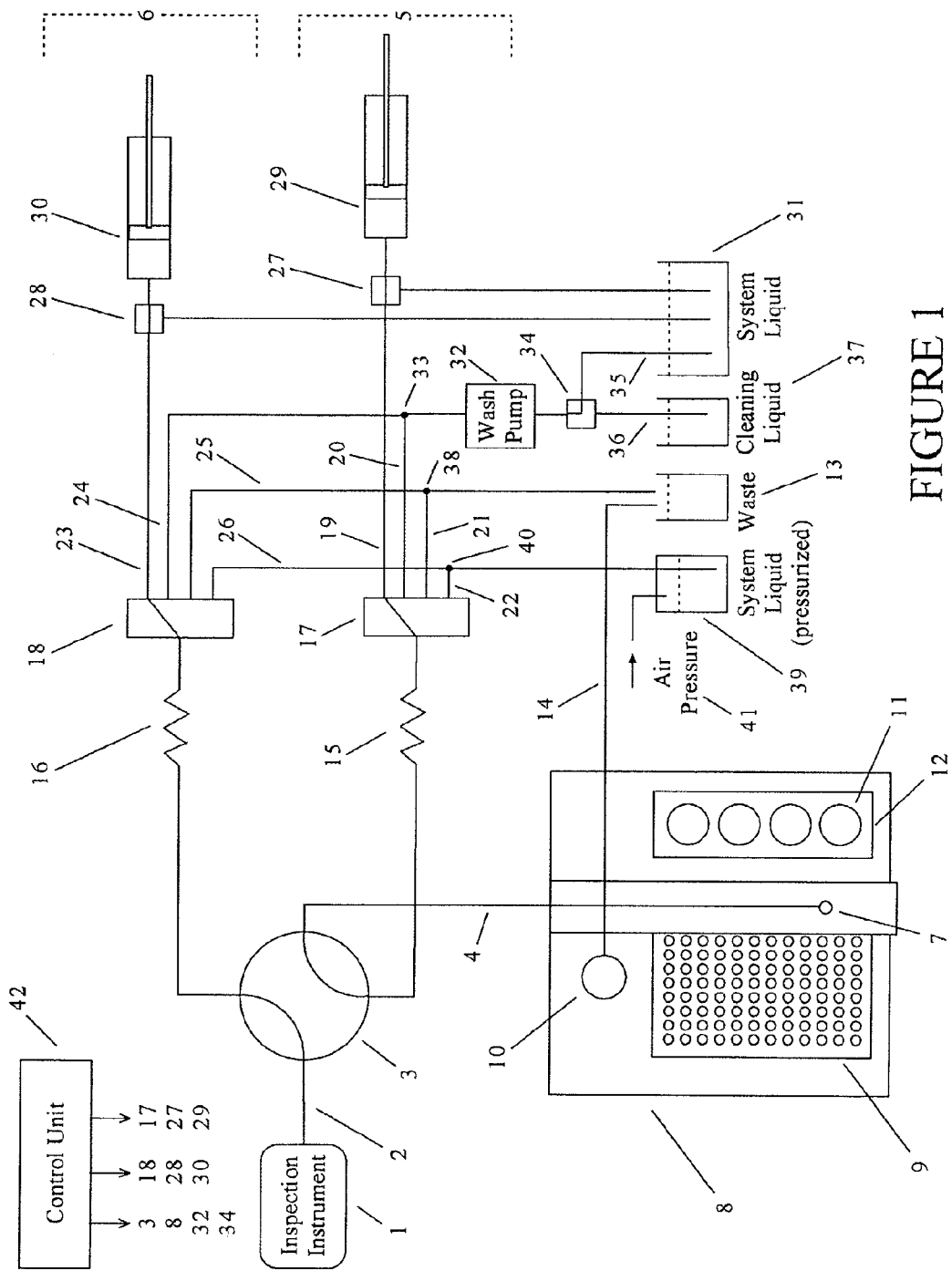
FIG. 1 is a diagram showing a configuration of one embodiment of the present invention.

FIG. 1 shows one embodiment of the present invention and is intended to be non-limiting in its scope. In FIG. 1, an inspection instrument (in this case a flow cytometer) 1 is in fluid communication with a four-way two position switching valve 3 via a flexible fluidic interface channel 2. The interface channel may be constructed of any known tubing material suitable for use with an inspection instrument. Non-limiting examples of tubing material for the interface channel and all other tubing materials involved in the present invention include tubing made from flexible silicon, polyvinyl chloride (PVC), polyether ether ketone (PEEK), polytetrafluoroethylene (PTFE), and any other useful polymeric materials, such as polyesters, polyolefins, or polyamides. The interface channel 2 may have an internal diameter from roughly about 0.005" to about 0.040", although other sizes of internal diameter may be appropriate depending on the inspection instrument used. The valve 3 switches sample input channel ("input channel") 4 and interface channel 2 between two symmetrical sample loading and injection branches of the system 5 and 6. In a first position of the switching valve 3, branch 5 is fluidicly coupled to input channel 4 and interface channel 2 (and thus, the inspection instrument 1) is fluidicly coupled to branch 6. When the valve 3 is switched into a second position (not shown), branch 5 would be fluidicly coupled to interface channel 2 (and thus, the inspection instrument 1) and input channel 4 would be fluidicly coupled to branch 6.

The other end of input channel 4 and is coupled to a probe 7, which is mechanically coupled to a positioning device 8. In one embodiment, the input channel comprises the probe and positioning device. The probe 7 provides the input channel 4 with an appropriate sample. Any type of sample that is analyzed with by an inspection instrument may be used in the present invention, including liquid, gaseous, or solid samples. Non-limiting examples of useful samples include chemical compounds and biological compounds. Some non-limiting examples of chemical compounds include chemical reagents, solvents, microspheres, beads, and dyes. Preferably, the chemical compounds comprise compounds that are known and used in an HPLC or a flow cytometer inspection instrument. Some non-limiting examples of biological compounds include blood, urine, antibodies, live cells, dead cells, and microorganisms. The cells may be from humans, animals, insects, bacteria, yeast, or viruses. Preferably, the biological compounds comprise compounds that are known and used in a flow cytometer inspection instrument.

The positioning device 8 may be any device known to one of ordinary skill in the art. The positioning device 8 may be commanded to move the probe 7. Non-limiting examples of positioning devices include a Cartesian robotic sampler and a rotary sampler. Another example of a positioning device 8 includes an XYZ positioning device, such as a Tecan MSP9250 robotic sampler with travel range of 15.4" on X axis, 11.8" on Y axis, and 6.5" on Z axis. The positioning accuracy of this device is 0.004" on all axes. The Z axis of positioning device 8 is capable of mounting probes of diameters up to 0.078" via a set screw. In another embodiment, the robotic sampler comprises separate arms for delivering a variety of reagents to the samples. In another embodiment, the robotic sampler comprises separate arms, for example, one, two, three, or four arms, for delivering a variety of samples to the inspection instrument. In another embodiment, the at least one sample input channel is coupled to a robotic sampler positioning device. In another embodiment, the robotic sampler comprises two arms and the second arm comprises a reagent transfer pump. In one embodiment, the second arm delivers a variety of reagents, for example, first and second reagents. In another embodiment, the reagent transfer pump comprises a syringe pump, a peristaltic pump, or a diaphragm pump.

Probe 7 may be any known tubing systems useful in the transportation of samples within the system. In one embodiment, probe 7 comprises a stainless steel tubing of about 0.072" outer diameter (OD), and about 0.063" inner diameter (ID), although other tubing dimensions are contemplated. For example, the OD of the probe may range between about 0.050" and 0.100" and ID of the probe may range between about 0.045" and about 0.095". A typical probe tubing length is about 4" but could be longer or shorter depending on the type of sample containers 9 and reagent vials 11 that are used. Preferably, probe 7 is long enough to be able to reach the bottom of sample containers 9 and reagent vials 11 without end of Z axis impacting top of the container. An additional 1" may be added to this minimum probe length to allow for mounting of probe 7 in the end of Z axis of positioning device 8.

In one embodiment, probe 7 has a rectangular opening machined into its side, starting about 1" from the end of probe 7 where it is mounted onto the Z axis of positioning device 8 and extending for about 0.5" from that point. The depth of this opening may be about one half of the outer diameter of the probe 7. Input channel 4 may pass through this opening and out of the tip of probe 7. The outer diameter of input channel 4 may be sized so that it snugly fits within the inner diameter of the probe 7. For example, the OD of input channel 4 may be about 0.0625" when the ID of the probe is 0.063" and the input channel 4 may optionally be friction fit into probe 7. Input channel 4 may be extended from the tip of probe 7 by approximately 0.5" to avoid contact between the outer wall of probe 7 and the contents of sample containers 9 where the sample containers are relatively flat, for example, a 96-well plate, a 385-well plate, or a 1536-well plates.

The positioning device 8 can be commanded to move probe 7 among several devices, including sample containers 9, a wash station 10, and any of the reagent vials 11 located in a reagent rack 12. Many different sample containers 9 may be employed in the embodiments described herein. Non-limiting examples of sample containers include tube racks comprising varying amounts of sample tubes and well plates of 96, 384, or 1536 wells.

In one embodiment, the wash station 10 is coupled to a waste reservoir 13 via a large bore drain channel 14. In another embodiment, the waste reservoir 13 is physically located below the wash station 10 to allow any liquids expelled into the wash station 10 to flow into the waste reservoir 13 under gravity. The waste station drain channel should have an internal diameter large enough to prevent airlock in the line upon drainage of any waste material. The typical internal diameter of a waste station drain channel 14 is not less than about ⅜ inches.

In an embodiment, both sample loading and injection branches 5 and 6 of the system are identical in configuration and are each independently controlled. In an embodiment, each branch 5 and 6 consists of a sample holding loop 15 and 16, respectively, control valves 17 and 18, respectively, channels 19 through 22 and 23 through 26, respectively, pump flow control valves 27 and 28, respectively, and pumps 29 and 30, respectively. In one embodiment, the sample holding loops 15 and 16 are fluidicly coupled to the switching valve 3. In an embodiment, the sample holding loops 15 and 16 are constructed of a length of tubing having internal volume greater than the maximum volume of sample that can be loaded and injected by the system. This ensures that the sample holding loops 15 and 16 have sufficient volume to contain any sample that may be injected therein.

The other end of each holding loop 15 and 16 is fluidically coupled to control valves 17 and 18 respectively. Typically, holding loops 15 and 16 would have internal volume one and one half times greater than the maximum volume of sample to prevent sample from being aspirated into control valves 17 and 18. In one embodiment, both control valves 17 and 18 are selection valves comprising four channels capable of coupling sample holding loops 15 and 16 to one of the four fluidic channels. For embodiments not requiring as many fluidic channels, the selection valves may comprise as few as two channels. In other embodiments, selection valves with more than four channels can be used in order to provide additional washing capabilities of the system.

Control valves 17 and 18 having multiple channels provide many advantageous features for the invention described herein. In FIG. 1, control valves 17 and 18 selectively connect sample holding loops 15 and 16 to one of four possible channels. Holding loop 15 is connected to channels 19, 20, 21, and 22 and holding loop 16 is connected to channels 23, 24, 25, and 26.

In an embodiment, the control valves 17 and 18 comprise channels for pumps. Pump channels 19 and 23 are connected to output ports of pump flow control valves 27 and 28 respectively. Pump flow control valves 27 and 28 are normal three way valves with a common port, a normally open port, and a normally closed port. The common ports of pump flow control valves 27 and 28 are connected to pumps 29 and 30, which are capable of aspirating and dispensing liquids. In an embodiment, pumps 29 and 30 are each independently a syringe pump. However, other types of pumps may be used. Non-limiting examples include peristaltic pumps and diaphragm pumps. In an embodiment, the input ports of pump flow control valves 27 and 28 are connected to a system liquid reservoir 31. Any system liquid useful in allowing or aiding performance of the inspection instrument may be used. Non-limiting examples include water, saline, or phosphate-buffered saline.

In an embodiment, the control valves 17 and 18 comprise channels for holding cleaning fluid to wash and clean the system. Wash channels 20 and 24 are both fluidically coupled to each other and a wash pump 32 at tee junction 33. The wash pump 32 is fluidically coupled to a common port of a three way wash liquid selection valve 34 that comprises a common port, a normally open port, and a normally closed port. The normally open port of valve 34 is connected to system liquid reservoir 31 via channel 35 and the normally closed port of valve 34 is connected to cleaning liquid reservoir 37 via channel 36. Wash pump 32 in this embodiment is a diaphragm pump capable of rapidly pumping cleaning liquids to control valves 17 and 18. Other non-limiting examples of suitable pumps that can be used for pumping liquids through the system include peristaltic, syringe, and a pressurized reservoir.

In an embodiment, the control valves 17 and 18 comprise channels for waste. Waste channels 21 and 25 are both fluidicly coupled to each other and a waste reservoir 13 at a tee junction 38.

In an embodiment, the control valves 17 and 18 comprise channels for controlling the pressure in the channels. Pressurized channels 22 and 26 are both fluidically coupled to each other and a pressurized system liquid reservoir 39 at a tee junction 40. The pressurized system liquid reservoir 39 is pressurized via a carefully controlled air pressure source 41. Controlled air pressure sources useful in the present invention include a regulated compressed air tank or a regulated air compressor. Alternatively, the pressure source may come from the inspection instrument 1 if such source is available. However, pressurized channels 22 and 26 are preferred when very precise measurements are to be taken and injecting samples with pumps 29 and 30 would increase the signal to noise ratio.

One improvement provided by the control valves 17 and 18 is the capability to rapidly wash lines 15 and 16 with a cleaning liquid 37. A sticky compound is any compound that remains in the lines of the system that has the potential to contaminate future samples. Often, sticky compounds, for example compounds such as sphingosine-1-phosphate (S1P), endothelin-1 (ET-1), and rhodamine, are involved when using inspection instruments, such as flow cytometers. It is therefore essential to clean system lines between sample inspections with a cleaning solution in order to eliminate any carryover that may exist from previous samples. Typical system liquids, such as saline solution, as compared to cleaning liquids, are prone to leave behind sticky compounds in the lines of the system. This causes contamination for hundreds of samples that are analyzed afterward.

Another feature of the control valves 17 and 18 is that they allow the inspection instrument 1 to back-flush remaining sample in interface line 2 back through the apparatus into waste. As sample travels through interface line 2 and lines 15 and 16, it becomes longer because sample in the center of the tube travels faster than at the surface. This often leads to a situation where the whole sample is never fully injected into the inspection instrument.

This may be accomplished by connecting line 2 to one of the lines 15 and 16 and also connecting control valves 17 and 18 to waste channels 21 and 25. Where a flow cytometer is used as the inspection instrument, it may pressurize the input line 2, making the connection to a waste line that is open to atmospheric pressure. This often causes a rapid flow of clean liquid from inspection instrument 1 through interface line 2. This feature makes it possible to carry out inspection of samples at high speed because it overcomes the problem of waiting for extended periods of time for sample to clear the tubing.

Another feature of the control valves 17 and 18 is that they allow the capability to load large sample volumes utilizing syringes 29 and 30. The large sample volumes may then be injected with high precision utilizing pressurized system liquid 39. This is particularly important as syringe size increases. As syringe size increases, the minimum flow rate that a syringe pump can sustain without fluctuations also increases. As the flow rate increases, the inspection instrument (particularly a flow cytometer) loses precision in measuring the samples. The present invention described herein allows one of ordinary skill in the art to load a large sample, such as 1 mL, 2 mL, or even greater, and then inject it very slowly allowing for the same precision found in manual tube injection, but with the additional advantage of full automation.

In another embodiment, the pressurized system liquid vessel 39 may be replaced with a high-resolution syringe pump. High-resolution syringe pumps are capable of supplying larger volumes of liquid at very low flow rate. Inserting a high-resolution syringe pump may be accomplished by replacement of the pressurized system liquid vessel 39.

The invention described herein provides the capability to deliver one or more reagents to sample containers before they are injected into the system by utilizing a separate auto-sampler arm comprising its own syringe for aspirating or dispensing. Such a feature would prevent carryover from sample containers back to the reagent if the auto-sampler arm carrying a reagent dispenses that reagent into the wells above the liquid surface of the sample. In an embodiment, the auto-sampler comprises multiple arms, such as an auto-sampler comprising two, three, or four arms. In another embodiment, the auto-sampler comprises two arms. Where cells are utilized as the reagent and a single same auto-sampler arm is used to take cells to the sample, mix and inject, and then go back to cells, it is possible that carryover of unwashed parts of the sample back to the cells may occur. One example where multiple reagents may be added to the sample before injection in the instrument comprises having agonist compounds on a plate well and adding cells to the well before they are injected into the inspection instrument. Other combinations of reagents and samples, as described herein, may be substituted for agonists and cells. Another example comprises placing an allosteric modulator or other antagonist compounds in a plate well, adding cells from a reagent vial, and then finally adding another agonist compound into the well. The mixture may then be injected into the flow cytometer. Each sample may have different types and varying numbers of reagents added thereto. In one embodiment, delivery of first and second reagents, and optionally additional reagents is performed with a separate auto-sampler arms.

In some embodiments, the channels comprising the system are made with polymer tubing having internal diameter of about 0.02 inches. In another embodiment, a PFA (PerFluoroAlkoxy) material is used to minimize any issues associated with gas permeability. Channels connected to the system liquid reservoir 31 are typically made with tubing having larger internal diameter such as about $\frac{1}{16}$ inches or about 0.094 inches. In another embodiment, the holding loops 15 and 16 are made out of larger internal diameter tubing if switching valve 3 and control valves 17 and 18 are in close physical proximity in order to reduce the required length of tubing.

In an embodiment, a control unit 42 is electrically connected to switching valve 3, positioning device 8, wash pump 32, wash liquid selection valve 34, control valves 17 and 18, pump flow control valves 27 and 28, and pumps 29 and 30. The control unit 42 is implemented as a computer capable of independent control of all attached devices. Control unit 42 may also set the air supply pressure 41 via an adjustable regulator. The air supply pressure can also be controlled via a manual pressure regulator. In an embodiment, the air supply pressure 41 is set to a value slightly higher than backpressure generated by inspection instrument 1. For example, the air supply pressure may be set to between about 0.5 and about 2.0 psi over the backpressure.

The operation of the foregoing apparatus having the above-described configuration will now be explained in some non-limiting embodiments. The control of the operation is preferably performed according to commands from control unit 42.

Initially, an operation is performed to fill all system channels (except for waste channels 21 and 25) with system liquid. Positioning device 8 is commanded to move the probe 7 into the wash station 10. The pump flow control valve 27 is switched to communicate system liquid from reservoir 31 to pump 29. Thereafter, pump 29 is filled with system liquid by command from control unit 42. The pump flow control valve 27 is then switched to communicate system liquid in pump 29 to pump channel 19. The valve 3 is switched into position to communicate liquid between input channel 4 and holding loop 15.

Next, control valve 17 is switched to communicate liquid between holding loop 15 and pump channel 19. The pump 29 is commanded to completely expel system liquid into pump channel 19 and holding loop 15 effectively purging air and filling both with the system liquid. Valve 17 is then switched to communicate liquid between holding loop 15 and wash channel 20, which connects to the wash pump 32. The wash liquid selection valve 34 is switched to fluidically couple the wash pump 32 and cleaning liquid reservoir 37 via cleaning liquid channel 36. Wash pump 32 is then turned on to fill cleaning liquid channel 36 with a cleaning liquid. Any cleaning liquid capable of removing sample residue and providing a non-contaminated surface for the channels may be selected. Some non-limiting examples of cleaning liquids include solvents such as ethanol, dimethyl sulfoxide (DMSO), or a detergent. Wash liquid selection valve 34 is then switched to fluidically couple wash pump 32 and system liquid reservoir 31 via channel 35. The system liquid fills wash pump 32, wash channel 20, control valve 17, holding loop 15, switching valve 3, input channel 4 and probe 7 with system liquid.

The wash pump 32 is then turned off after a fixed delay sufficient to fill components mentioned above with the system liquid. If pressurized system liquid reservoir 39 is connected to control valve 17, then valve 17 is switched to communicate the pressurized system liquid from reservoir 39 to holding loop 15 via pressurized channel 22. After a delay to fill pressurized channel 22 with system liquid, control valve 17 is switched to communicate liquid in holding loop 15 to the waste channel 21.

In order to fill the second branch of the system with system liquid, valve 3 is switched into position to communicate liquid between input channel 4 and holding loop 16. The sequence of events described above for the first branch of the system is then repeated for the equivalent parts of the second branch of the system. The resulting state of the system is with probe 7 in wash station 10 and all channels of the system (except waste channels 21 and 25) filled with system liquid. In another embodiment, the process of filling lines with system liquids may further be practiced with additional branches.

Figure 2A:
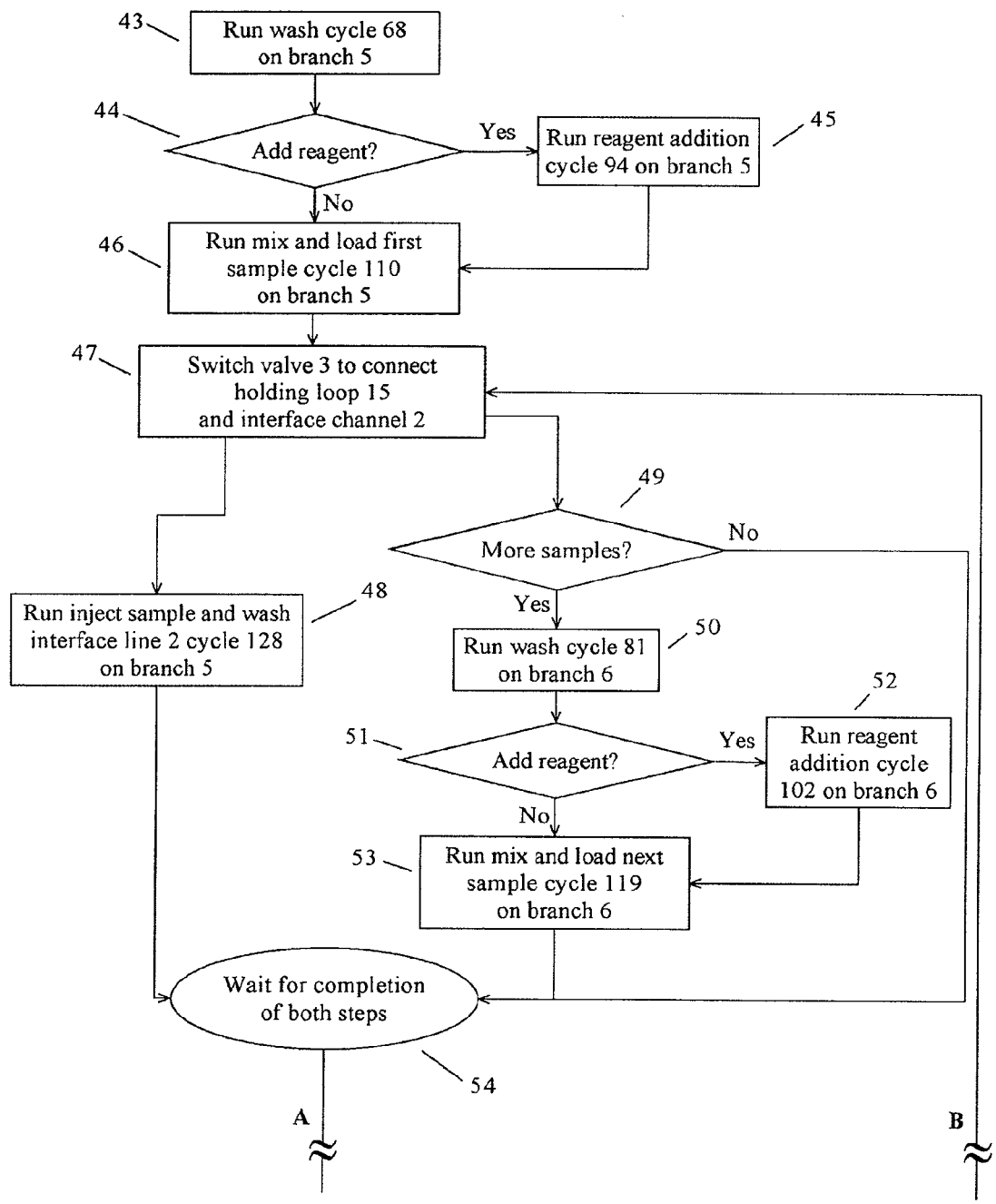
FIGS. 2A and 2B show a top level diagram showing an embodiment of one operation of the control unit.
Figure 2B:
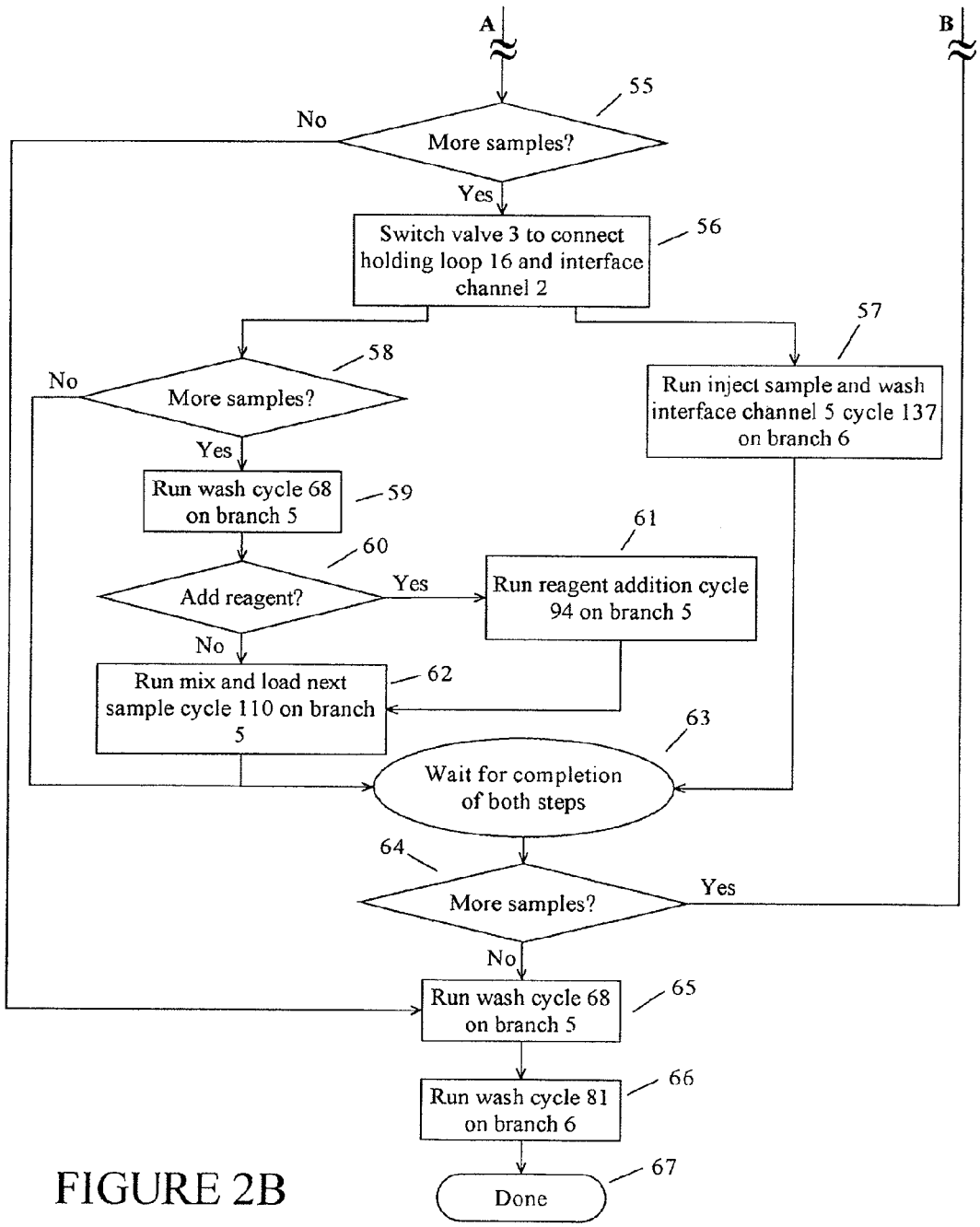

FIGS. 2A and 2B show another embodiment of the present invention and are intended to be non-limiting in its scope. FIGS. 2A and 2B show a sequence of steps to evaluate one or more samples from sample containers 9. In step 43, which is the starting point of FIG. 2A, a wash cycle 68 (further described in FIG. 3) is executed on branch 5. Wash cycle 68 ensures that branch 5 has been washed and is filled with system liquid. In some embodiments, it may be beneficial to add a reagent to sample containers 9 before the sample is analyzed. Examples of non-limiting reagents include agonists, antagonists, modulators, dyes, stains, cells, and beads. Where a user selects to add a reagent to the sample in step 44, a reagent addition cycle 94 is executed on branch 5 in step 45. In step 46, the first sample is loaded into holding loop 15 by executing mix and load next sample cycle 110 (further described in FIG. 5) on branch 5. In step 47, switching valve 3 is switched to fluidicly couple holding loop 15 and interface channel 2. Two concurrent and independent processes are then executed. The first process comprises step 48 and the second process comprises steps 49 through 53.

In the first process, a sample is injected into the inspection instrument 1 and the interface channel 2 is washed in step 48 by running inject sample and wash interface line cycle 128 (further described in FIG. 6A) on branch 5. The second process first determines if there are any more samples left to be processed in step 49. If all of the samples have been processed, the second process terminates by going to step 54. Otherwise branch 6 is washed in step 50 by executing a wash cycle 81 (further described in FIG. 3). If the user selected to add a reagent to the sample in step 51, a reagent addition cycle 102 (further described in FIG. 4) is executed on branch 6 in step 52. In step 53, the next sample is loaded into holding loop 16 by executing mix and load next sample cycle 119 (further described in FIG. 5) on branch 6. Upon completion of both processes in step 54, a check is made in step 55, shown in FIG. 2B, to determine if all samples have been processed. If no more samples remain, then the execution continues at step 65.

If there are still samples to be processed, switching valve 3 is switched to fluidicly couple holding loop 16 and interface channel 2 in step 56. Two concurrent and independent processes are then executed. The first process comprises step 57 and the second process comprises steps 58 through 62.

The first process injects sample into inspection instrument 1 and washes interface channel 2 in step 57 by running inject sample and wash interface line cycle 137 (further described in FIG. 6B) on branch 6. The second process first determines if there are any more samples left to be processed in step 58. If all samples have been processed, then the second process terminates by going to step 63. Otherwise branch 5 is washed in step 59 by executing a wash cycle 68. If the user selected to add a reagent to the sample in step 60, a reagent addition cycle 94 is executed on branch 5 in step 61. In step 62, the next sample is loaded into holding loop 15 by executing mix and load next sample cycle 110 (further described in FIG. 5) on branch 5. Upon completion of both processes in step 63 a check is made in step 64 to determine if all samples have been processed. If no more samples remain the execution continues at step 65, otherwise execution continues at step 47 described above.

In step 65, branch 5 is washed by executing wash cycle 68. Then, branch 6 is washed by executing wash cycle 81 in step 66. Sample processing completes in step 67 with the system in a ready state to start processing another set of samples upon replacement of sample containers 9.

Figure 3:
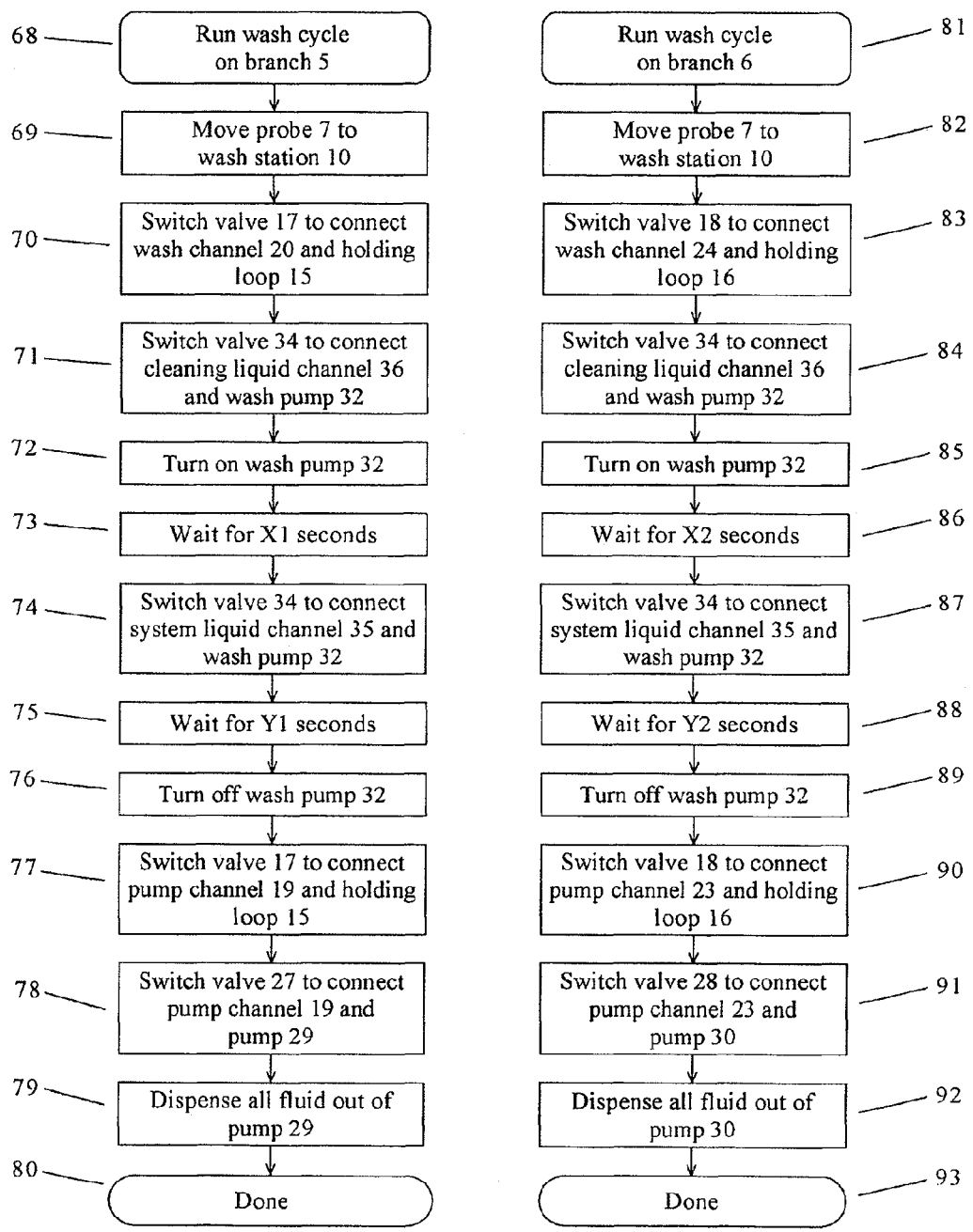
FIG. 3 is a diagram showing an embodiment of one sequence of control unit commands for washing both branches of the system.

FIG. 3 shows another embodiment of the present invention and is intended to be non-limiting in its scope. FIG. 3 shows a sequence of steps wherein both branches of the system described herein are washed. The initial wash cycle 68 begins by moving probe 7 to wash station 10 in step 69. In step 70, control valve 17 is switched to connect wash channel 20 to holding loop 15. In some embodiments, samples to be introduced into the inspection instrument 1 may be hydrophobic and prone to sticking to the channel walls. It is often necessary to wash the channels with a cleaning liquid to reduce chances of cross contamination from one sample to the next. Any cleaning liquid capable of removing sample residue and providing a non-contaminated surface for the channels may be selected. Some non-limiting examples of cleaning liquids include solvents such as ethanol, dimethyl sulfoxide (DMSO), or a detergent.

In step 71, the wash liquid selection valve 34 is switched to connect cleaning liquid channel 36 and wash pump 32. The wash pump 32 is then turned on in step 72 to pump cleaning fluids into the control valves. A user specified delay of X1 seconds is introduced at step 73 to allow cleaning liquid to be pumped all the way through valve 17, holding loop 15, switching valve 3, input channel 4 and probe 7 into wash station 10. The actual amount of time needed may vary depending on the system being used and the length of the channels. One of ordinary skill in the art, guided by the disclosure provided herein, can determine how much time will be required for the cleaning liquids to be pumped throughout the system.

With the wash pump 32 still running, the wash liquid selection valve 34 is switched to connect channel 35 to the wash pump 32, as shown in step 74. This action establishes a flow of system liquid from system liquid reservoir 31 through the wash pump 32. A user specified delay of Y1 seconds is introduced at step 75 to allow system liquid to be pumped all the way through valve 17, holding loop 15, switching valve 3, input channel 4 and probe 7 into wash station 10, thus washing out all remaining cleaning liquid. The actual amount of time needed may vary depending on the system being used and the length of the channels. One of ordinary skill in the art, guided by the disclosure provided herein, can determine how much time will be required to wash out the cleaning liquids.

Wash pump 32 is turned off in step 76 and control valve 17 is switched to connect pump channel 19 and holding loop 15 in step 77. In step 78, pump flow control valve 27 is switched to connect pump channel 19 and pump 29. All fluid is then expelled out of pump 29 in step 79. Step 80 shows the completion of wash cycle 68.

The wash cycle 81 for branch 6 of the system is the same as wash cycle 68 for branch 5 with all elements of branch 5 replaced with corresponding elements of branch 6. The wash cycle 81 is illustrated in steps 82 through 93. The initial wash cycle 81 begins by moving probe 7 to wash station 10 in step 82. In step 83, control valve 18 is switched to connect wash channel 24 to holding loop 16. As previously stated in regards to wash cycle 68, some embodiments involve samples introduced into the inspection instrument 1 that are hydrophobic and prone to sticking to the channel walls. Similar cleaning liquids may be used in regards to wash cycle 81 that are useful in regards to wash cycle 68.

In step 84, the wash liquid selection valve 34 is switched to connect cleaning liquid channel 36 and wash pump 32. The wash pump 32 is then turned on in step 85 to pump cleaning fluids into the control valves. A user specified delay of X2 seconds is introduced at step 86 to allow cleaning liquid to be pumped all the way through valve 18, holding loop 16, switching valve 3, input channel 4 and probe 7 into wash station 10. The amount of X2 seconds used in step 86 may be the same or different from the amount of time used in step 73 for wash cycle 68 on branch 5. One of ordinary skill in the art, guided by the disclosure provided herein, can determine how much time will be required for the cleaning liquids to be pumped through the system.

With the wash pump 32 still running, the wash liquid selection valve 34 is switched to connect channel 35 to the wash pump 32, as shown in step 87. This action establishes a flow of system liquid from system liquid reservoir 31 through the wash pump 32. A user specified delay of Y2 seconds is introduced at step 88 to allow system liquid to be pumped all the way through valve 18, holding loop 16, switching valve 3, input channel 4 and probe 7 into wash station 10, removing all of the remaining cleaning liquid. The actual amount of time needed may vary depending on the system being used and the length of the channels. The amount of Y2 seconds used in step 88 may be the same or different from the amount of time used in step 75 for wash cycle 68 on branch 5. One of ordinary skill in the art, guided by the disclosure provided herein, can determine how much time will be required to wash out the cleaning liquids.

Wash pump 32 is turned off in step 89 and control valve 18 is switched to connect pump channel 23 and holding loop 16 in step 90. In step 91, pump flow control valve 28 is switched to connect pump channel 23 and pump 30. All fluid is then expelled out of pump 30 in step 92. Step 93 shows the completion of wash cycle 81.

Figure 4:
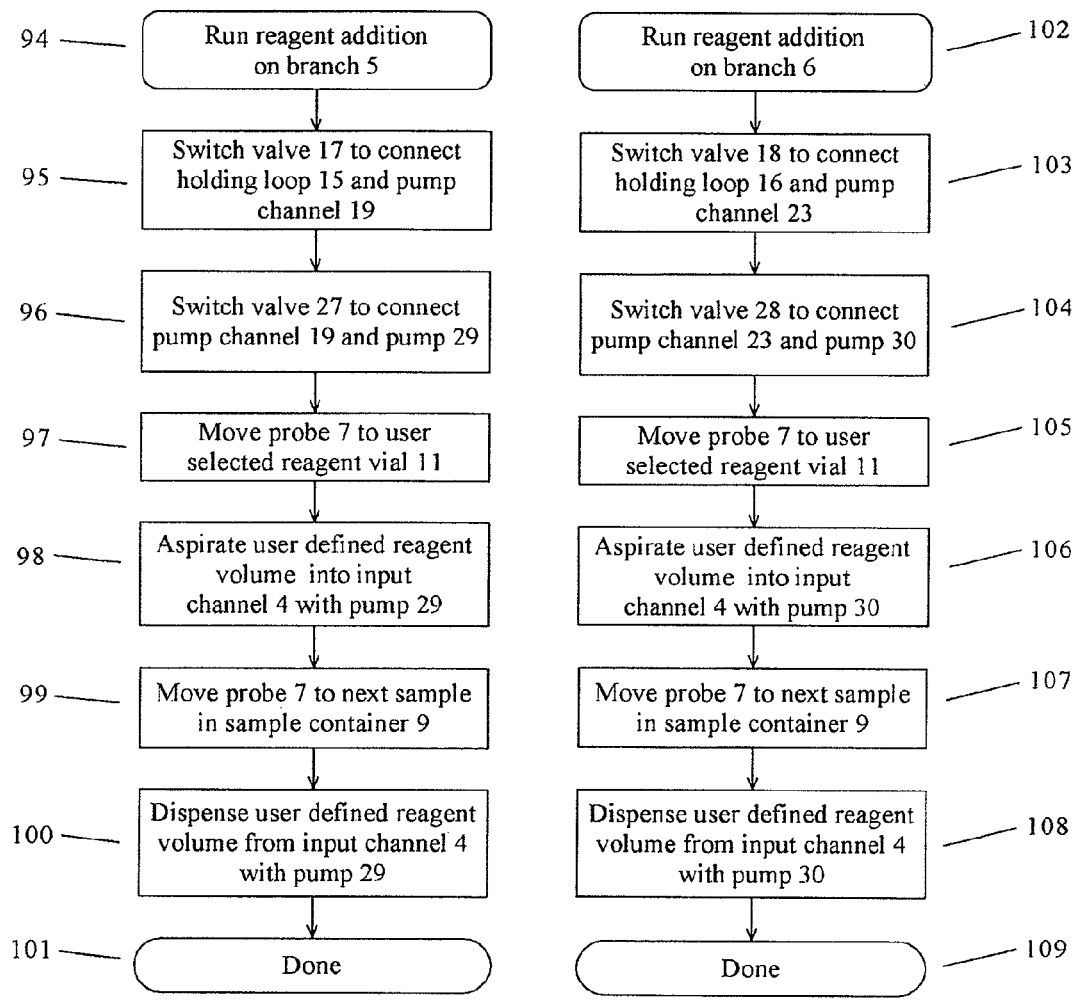
FIG. 4 is a diagram showing an embodiment of one sequence of control unit commands for adding a reagent to sample containers on both branches of the system.

FIG. 4 shows another embodiment of the present invention and is intended to be non-limiting in its scope. In FIG. 4, a sequence of steps to add reagent on both branches of the system is described. Reagent addition cycle 94 starts by switching control valve 17 to connect holding loop 15 and pump channel 19 in step 95. Then in step 96, pump flow control valve 27 is switched to connect pump channel 19 and pump 29. The probe 7 is then moved to a user selected reagent vial 11 in step 97. A volume of reagent is aspirated into probe 7 and input channel 4 by issuing an aspirate command to pump 29 in step 98. The volume of reagent aspirated into the probe and probe 7 and input channel 4 is selected by the user of the system and may be any amount necessary to complete the relevant tests.

The probe 7 is then moved from the reagent vial into the sample container of the next sample to be loaded in step 99. The reagent is then dispensed into sample from input channel 4 by issuing a dispense command to pump 29 in step 100. Reagent addition cycle 94 is shown as completed in step 101.

Reagent addition cycle 102 for branch 6 of the system is the same as reagent addition cycle 94 for branch 5 with all elements of branch 5 replaced with corresponding elements of branch 6. The reagent addition cycle 102 is illustrated in steps 103 through 109. Reagent addition cycle 102 starts by switching control valve 18 to connect holding loop 16 and pump channel 23 in step 103. Then in step 104, pump flow control valve 28 is switched to connect pump channel 23 and pump 30. The probe 7 is then moved to a user selected reagent vial 11 in step 105. A volume of reagent is aspirated into probe 7 and input channel 4 by issuing an aspirate command to pump 30 in step 106. The volume of reagent aspirated into the probe and probe 7 and input channel 4 is selected by the user of the system and may be any amount necessary to complete the relevant tests.

The probe 7 is then moved from the reagent vial into the sample container of the next sample to be loaded in step 107. The reagent is then dispensed into sample from input channel 4 by issuing a dispense command to pump 30 in step 108. Reagent addition cycle 102 is shown as completed in step 109.

Figure 5:
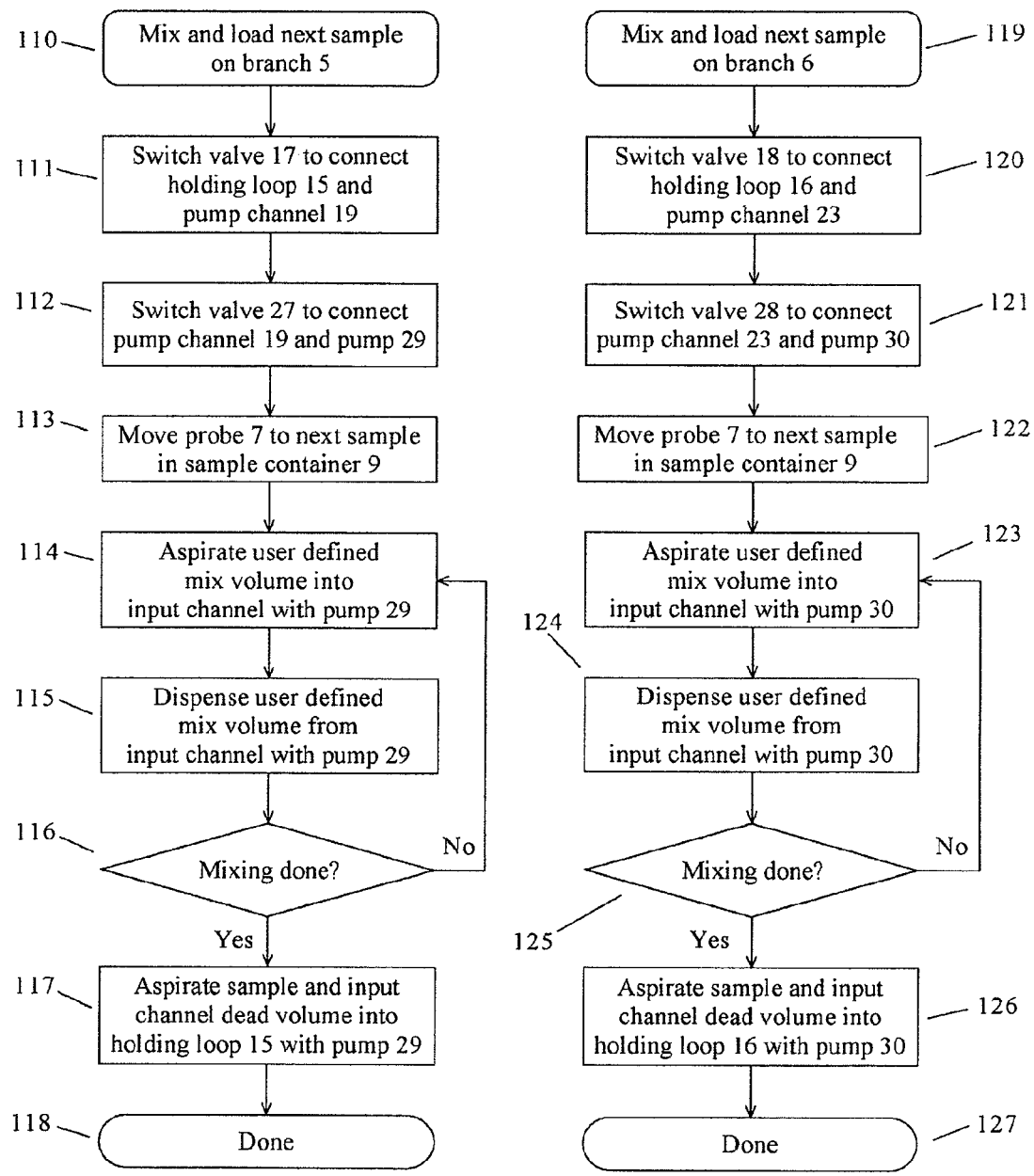
FIG. 5 is a diagram showing an embodiment of one sequence of control unit commands for mixing and loading samples on both branches of the system.

FIG. 5 shows another embodiment of the present invention and is intended to be non-limiting in its scope. In FIG. 5, a sequence of steps to mix and load the next sample on both branches of the system is described. For some types of samples, such as living cells or beads that may settle at the bottom of sample containers 9, it may be desired to mix the sample several times before aspirating it into holding loop 70. Mix and load next sample cycle 110 begins by switching control valve 17 to connect holding loop 15 and pump channel 19 in step 111. In step 112, pump flow control valve 27 is switched to connect pump channel 19 and pump 29. The probe 7 is then moved into a sample container 9 of the next sample to be loaded in step 113. A user defined sample mix volume is aspirated into the probe 7 and input channel 4 by issuing an aspirate command to pump 29 in step 114. The sample is then dispensed back into sample container 9 by issuing a dispense command to pump 29 in step 115.

The system user is able to define any number of mixing cycles necessary to complete the desired testing. If the user defined number of mixing cycles has not been completed in step 116 then execution repeats from step 114. Otherwise, a user defined sample volume and input channel dead volume is aspirated into holding loop 15 with pump 29 in step 117. The mix and load next sample cycle 110 is shown as completed in step 118.

Mix and load next sample cycle 119 for branch 6 of the system is the same as mix and load next sample cycle 110 for branch 5 with all elements of branch 5 replaced with corresponding elements of branch 6. The mix and load next sample cycle 119 is illustrated in steps 120 through 127. Mix and load next sample cycle 119 begins by switching control valve 18 to connect holding loop 16 and pump channel 23 in step 120. In step 121, pump flow control valve 28 is switched to connect pump channel 23 and pump 30. The probe 7 is then moved into a sample container 9 of the next sample to be loaded in step 122. A user defined sample mix volume is aspirated into the probe 7 and input channel 4 by issuing an aspirate command to pump 30 in step 123. The sample is then dispensed back into sample container 9 by issuing a dispense command to pump 30 in step 124.

The system user is able to define any number of mixing cycles necessary to complete the desired testing. If the user defined number of mixing cycles has not been completed in step 125 then execution repeats from step 123. Otherwise, a user defined sample volume and input channel dead volume is aspirated into holding loop 16 with pump 30 in step 126. The mix and load next sample cycle 119 is shown as completed in step 127.

Figure 6A:
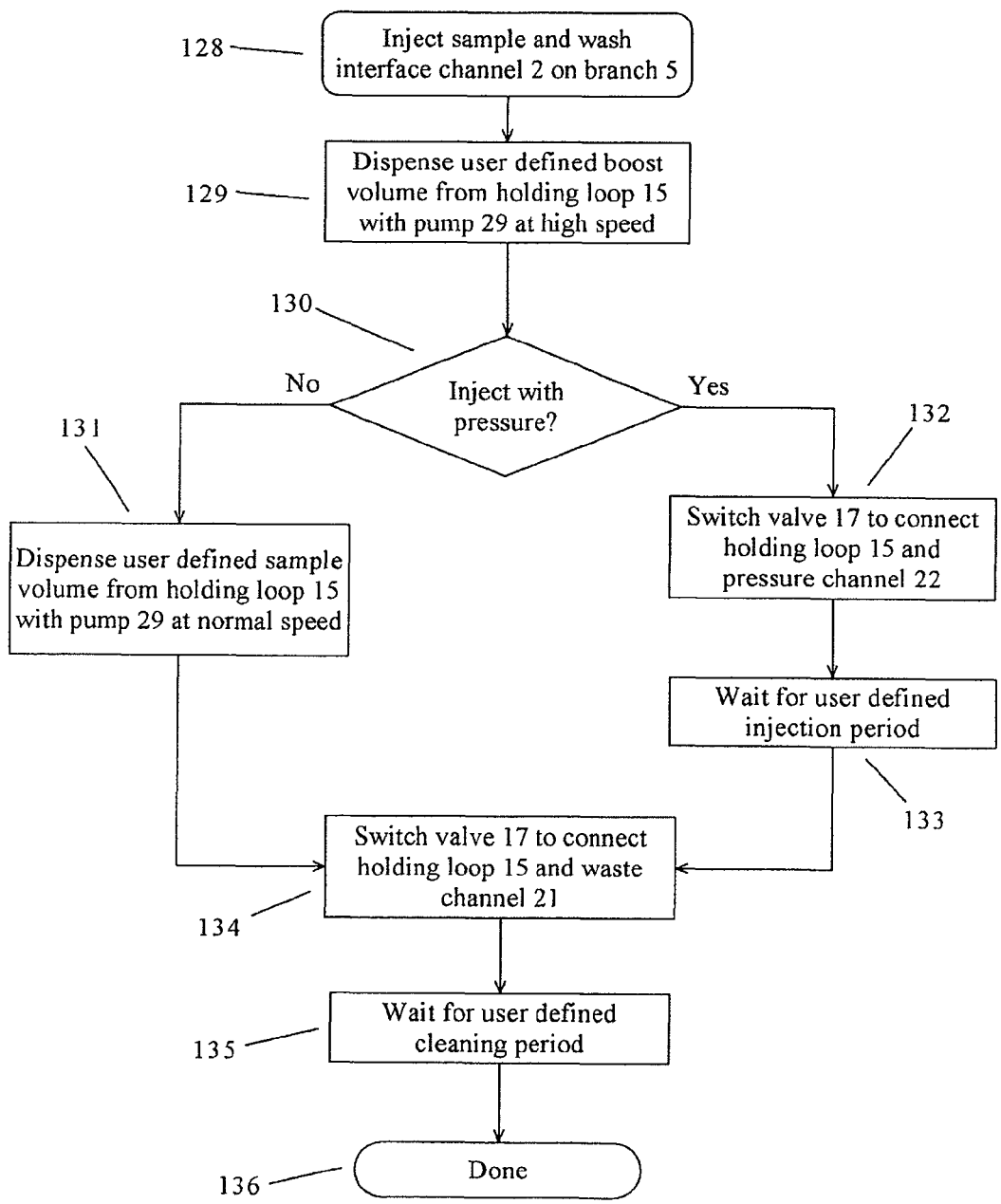
FIGS. 6A and 6B show a diagram showing an embodiment of one sequence of control unit commands for injecting sample and washing interface line on both branches of the system.
Figure 6B:
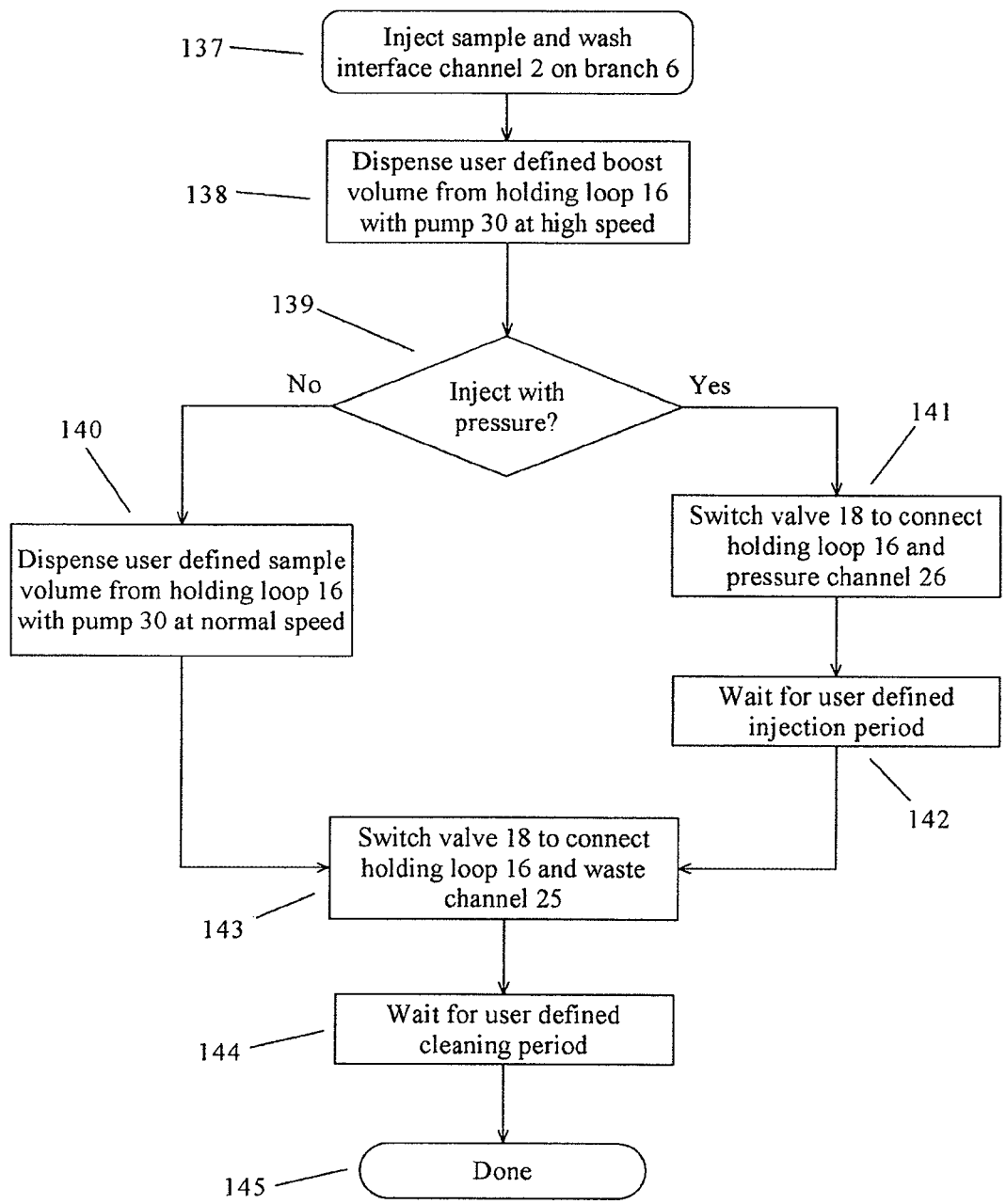

FIGS. 6A and 6B show another embodiment of the present invention and are intended to be non-limiting in its scope. In FIG. 6A, a sequence of steps to inject the sample and wash interface line 2 on both branches of the system is described. The inject sample and wash interface line cycle begins at step 128. After a sample is injected into the inspection instrument 1, the time in which it takes the sample to traverse interface channel 2 may be significant. This is especially true if the inspection instrument 1 is a flow cytometer, where rates can be as slow as approximately 1 µL/sec. To reduce time for sample injection, a user defined boost volume corresponding to internal volume of interface channel 2 is expelled from the holding loop 15 into inspection instrument 1 at a high speed in step 129. For example, the rate at which the sample is injected into the inspection instrument may be as high as about 10 µL/sec or greater. In another embodiment, the rate at which the sample is injected into the inspection instrument may be as high as about 50 µL/sec or greater. In still another embodiment, the rate at which the sample is injected into the inspection instrument may be as high as about 100 µL/sec or greater. This effectively brings the front of the sample plug into the inspection instrument 1 in a short amount of time.

The injection may be made either with pressure or without pressure. In step 130, if a user did not select to use a pressurized sample delivery, then the sample is injected into inspection instrument 1 by dispensing a user defined sample volume with pump 29 at normal speed in step 131. Otherwise steps 132 and 133 are executed. In step 132, control valve 17 is switched to connect holding loop 15 and pressurized channel 22. The user may specify a delay sufficient to inject the sample into the inspection instrument in step 133. In step 134, control valve 17 is switched to connect holding loop 15 and waste channel 21. The user may specify a cleaning delay in step 135 to allow back pressure from inspection instrument 1 to backwash interface channel 2 into the waste reservoir 13. Inject sample and wash interface line cycle 128 is completed as shown in step 136.

FIG. 6B shows inject sample and wash interface line cycle 137 for branch 6 of the system and is the same as inject sample and wash interface line cycle 128 for branch 5 with all elements of branch 5 replaced with corresponding elements of branch 6. The inject sample and wash interface line cycle 137 is illustrated in steps 138 through 145. A user defined boost volume corresponding to internal volume of interface channel 2 is expelled from the holding loop 16 into inspection instrument 1 at a high speed in step 138. For example, the rate at which the sample is injected into the inspection instrument may be as high as about 10 µL/sec or greater. In another embodiment, the rate at which the sample is injected into the inspection instrument may be as high as about 50 µL/sec or greater. In still another embodiment, the rate at which the sample is injected into the inspection instrument may be as high as about 100 µL/sec or greater. This effectively brings the front of the sample plug into the inspection instrument 1 in a short amount of time.

The injection may be made either with pressure or without pressure. In step 139, if a user did not select to use a pressurized sample delivery, then the sample is injected into inspection instrument 1 by dispensing a user defined sample volume with pump 30 at normal speed in step 140. Otherwise steps 141 and 142 are executed. In step 141, control valve 18 is switched to connect holding loop 16 and pressurized channel 26. The user may specify a delay sufficient to inject the sample into the inspection instrument in step 142. In step 143, control valve 18 is switched to connect holding loop 16 and waste channel 25. The user may specify a cleaning delay in step 144 to allow back pressure from inspection instrument 1 to backwash interface channel 2 into the waste reservoir 13. Inject sample and wash interface line cycle 137 is completed as shown in step 145.

The high-speed sample supply device disclosed herein is useful to deliver samples to any type of inspection instrument. Preferably, the device disclosed herein is used to delivery samples to a flow cytometer. Flow cytometers are well-known analytical tools that are able to analyze several thousand particles every second and can actively separate and isolate particles having specified properties. For example, the high-speed sample supply device may be used in flow cytometers described in U.S. Pat. Nos. 6,713,019; 5,824,269; 5,367,474; 5,135,502; and 4,702,598; all of which are hereby incorporated by reference in their entirety.

All patents incorporated by reference herein are incorporated by reference herein only with respect to the particular embodiments, materials, processes of manufacture and methods of use described therein. These patent are not to be considered incorporated by reference to the extent any of these patents expresses an opinion or presents any representation, characterization, or definition (either expressly or by implication) that is inconsistent with the opinions, representations, characterizations or definitions expressly made herein.

While there have been described herein what are to be considered exemplary and preferred embodiments of the present invention, other modifications of the invention will become apparent to those skilled in the art from the teachings herein. It is therefore desired to be secured in the appended claims all such modifications as fall within the true spirit and scope of the invention. Accordingly, what is desired to be secured by Letters Patent is the invention as defined and differentiated in the following claims.

What is claimed is:

1. A method for multiplexed sample analysis, comprising:
   (a) robotically obtaining a first liquid sample from the first of a plurality of sample sources;
   (b) switching a switching valve to fluidically couple the first liquid sample to an instrument;
   (c) delivering the first liquid sample through a first sample delivery line to the instrument for analysis of the sample, wherein a first control valve is located within the first sample delivery line;
   (d) robotically obtaining a second liquid sample from the second of a plurality of sample sources;
   (e) switching the switching valve to fluidically couple the second liquid sample to the instrument;
   (f) delivering the second liquid sample through a second sample delivery line to the instrument for analysis, wherein a second control valve is located within the second sample delivery line;
   (g) cleaning the first sample delivery line while the second sample delivery line is delivering sample to the instrument, wherein cleaning the first sample delivery line comprises:
      switching the first control valve to communicate liquid between the first sample delivery line and a wash channel fluidically coupled to a wash container comprising cleaning liquid; and
      switching the first control valve to communicate liquid between the first sample delivery line and a waste channel; and
   (h) cleaning the second sample delivery line while the first sample delivery line is delivering sample to the instrument, wherein the cleaning the second sample delivery line comprises:
      switching the second control valve located in the second sample delivery line to communicate liquid between the second sample delivery line and the wash channel; and
      switching the second control valve located in the second sample delivery line to communicate liquid between the second sample delivery line and the waste channel.

2. The method of claim 1, further comprising:
(i) repeating steps (a)-(h) to obtain and deliver multiple samples to the instrument from all of the plurality of sample sources.

3. The method of claim 1, wherein the instrument is a flow cytometer.

4. The method of claim 1, wherein the first and second liquid samples are independently selected from the group consisting of chemical compounds, antibodies, beads, live cells, or fixed cells.

5. The method of claim 1, further comprising the steps of:
delivering a first reagent to the first liquid sample before the sample is delivered to the instrument; and
delivering a second reagent to the second liquid sample before the sample is delivered to the instrument.

6. The method of claim 5, wherein the first and second reagents are independently selected from the group consisting of chemical compounds, antibodies, beads, live cells, or fixed cells.

7. The method of claim 5, wherein multiple reagents are added to the sample before the sample is injected into the instrument.

8. The method of claim 1, a pressurized channel is connected to the first and second control valves.

* * * * *